United States Patent [19]

Listemann

[11] Patent Number: 5,023,375

[45] Date of Patent: * Jun. 11, 1991

[54] PROCESS FOR THE SYNTHESIS OF AMIDES FROM VINYL ACETATE

[75] Inventor: Mark L. Listemann, Whitehall, Pa.

[73] Assignee: Air Products and Chemicals, Inc., Allentown, Pa.

[*] Notice: The portion of the term of this patent subsequent to Nov. 6, 2007 has been disclaimed.

[21] Appl. No.: 466,527

[22] Filed: Jan. 17, 1990

[51] Int. Cl.$^5$ .................. C07C 233/00; C07C 235/00; C07C 237/00; C07C 239/00
[52] U.S. Cl. .................................... 564/159; 564/137
[58] Field of Search ............................... 564/159, 137

[56] References Cited

U.S. PATENT DOCUMENTS

| | | | |
|---|---|---|---|
| 3,188,319 | 6/1965 | Smidt et al. | 548/479 |
| 4,018,826 | 4/1977 | Glass, Jr. et al. | 525/418 |
| 4,176,136 | 11/1979 | Brenzel | 564/159 |
| 4,322,271 | 3/1982 | Jensen et al. | 204/73 R |
| 4,425,277 | 1/1984 | Kawamoto et al. | 260/410.9 N |
| 4,490,557 | 12/1984 | Dawson et al. | 564/199 |
| 4,567,300 | 1/1986 | Murao et al. | 564/215 |
| 4,578,515 | 3/1986 | Dawson et al. | 564/215 |
| 4,670,591 | 6/1987 | Oftring et al. | 564/224 |
| 4,968,841 | 11/1990 | Listemann | 564/159 |

FOREIGN PATENT DOCUMENTS

| | | | |
|---|---|---|---|
| 2441526 | 3/1976 | Fed. Rep. of Germany | 564/159 |
| 3443463 | 5/1986 | Fed. Rep. of Germany | |
| 2188625 | 10/1987 | United Kingdom | 564/159 |

OTHER PUBLICATIONS

D. J. Dawson et al., "Poly(vinylamine Hydrochloride), Synthesis and Utilization for the Preparation of Water-Soluble Polymeric Dyes", JACS, 98, pp. 5996–6000, (1976).

J. A. Krimmel et al., "The Synthesis of Fluorine-Containing Aliphatic Gem-Dinitramines", Journal of Organic Chemistry, vol. 36, No. 2, p. 351 (1971).

R. H. Summerville et al., "Synthesis of N-Vinyl Acetamide and Preparation of Some Polymers and Copolymers", ACS, Polymer Preprints (1983), 24, pp. 12–13.

S. Takase et al., "The Reaction of Vinyl Acetate with Fatty Amide", Paper submitted to the Inst. of Chemistry, Coll. of Gen. Ed., Osaka Univ., (Rec. Oct. 11, 1967).

P. Busse et al., "Platinum (II) Catalyzed Alkoxide Exchange and Isomerization of Vinyl Ethers", Journal of Organometallic Chemistry, 140, (1977), pp. 229–236.

E. Bayer et al., "Honogeneous Catalytic Vinylation of Cyclic Imides and Lactams for the Synthesis of N-Vinyl Monomers", Angew. Chem. Int. Ed. Engl. (1979) 18(7), pp. 533–534.

Noyes et al., "Aldehyde-Amide Condensation, I. Reactions between Aldehyde and Acetamide", *American Chem. Soc. Journal*, vol. 55, pp. 3493–3494 (1933).

Adelman, "The Interchange Reaction of Vinyl Acetate With Organic Acids", *J. Org. Chem.*, vol. 14, pp. 1057–1077 (1949).

Furukawa et al., "Reaction of Vinyl Ethers with Acidic Imino Compounds, a New Synthesis of Some N-Vinyl Imides", *J. Org. Chem.*, vol. 23, pp. 672–676 (1958).

*Primary Examiner*—Glennon H. Hollrah
*Assistant Examiner*—Scott C. Rand
*Attorney, Agent, or Firm*—Mark L. Rodgers; William F. Marsh; James C. Simmons

[57] ABSTRACT

Ethylidene bisamide is produced by the reaction of vinyl acetate with a primary carboxylic acid amide over a catalytic amount of a salt of palladium (II), platinum-(II) or mercury(II). The reaction is carried out in the presence of an aliphatic or arylaliphatic alcohol in a concentration greater than 0.01 equivalents based upon the limiting reagent.

18 Claims, No Drawings

PROCESS FOR THE SYNTHESIS OF AMIDES FROM VINYL ACETATE

TECHNICAL FIELD

The present invention relates to the synthesis of amides by the reaction of vinyl acetate with formamide.

BACKGROUND OF THE INVENTION

Poly(vinylamines) are polymers which can be prepared over a broad range of molecular weights. Depending upon their average molecular weight, such polymers find various uses in the preparation of dyes, pharmaceuticals, flocculation agents and as viscosifiers in papermaking and enhanced recovery of oil. Because vinylamines are too unstable to be polymerized, these polymers are prepared by hydrolysis of poly(N-vinylamides) such as poly(N-vinylacetamide). The monomer for this polymer is made by the reaction of acetamide and acetaldehyde to form ethylidene bisacetamide which is then pyrolyzed to the N-vinylacetamide. This reaction is described in Dawson, et. al. *JACS*, 98, pg. 5996-6000 (1976). An improvement in the basic process is described as a reaction between acetamide and acetaldehyde over a sulfuric acid catalyst, rather than perchloric acid, in order to form ethylidene bisacetamide which was then pyrolyzed to form N-vinylacetamide. The N-vinylacetamide was polymerized and the polymer subjected to hydrolysis to form poly(vinylamine hydrochloride) which was used in preparing polymeric azo dyes.

U.S. Pat. No. 4,018,826 (1977) also discloses a method of making poly(vinylamine) by hydrolyzing poly(N-vinylacetamide) which has been formed by thermally cracking ethylidene bisacetamide prepared by reacting acetaldehyde and acetamide using an aqueous mineral acid catalyst.

It was known that a similar reaction could take place between formamide and acetaldehyde in an aqueous solution of hydrochloric acid as described in *Journal of Organic Chemistry*, Volume 36, No. 2, pg. 351 (1971), which describes a method for making 1,1-Bis(formamido)ethane, another name for ethylidene bisformamide.

U.S. Pat. No. 4,490,557 (1984) discloses the preparation of ethylidene bisformamide from acetaldehyde and formamide using an acidic catalyst and an ammonia scavenger, such as acetic anhydride. Wiped film evaporation is used to recover the ethylidene bisformamide which can be cracked to form N-vinylformamide, a monomer useful in preparing poly(N-vinylformamide) which can then be hydrolyzed to poly(vinylamines), useful in making dyes and pharmaceuticals. The acidic catalysts which are disclosed include acidic ion exchange resins, of which several examples are given including the preferred operating example. Alternatively, mineral acids, such as sulfuric or hydrochloric acid, or lower alkanoic acids, such as formic or acetic acids, can be used when added in catalytically effective amounts.

Because of the difficulty in recovering polymerization grade monomers by the above described routes, others have sought to prepare N-vinylcarboxylic acid amides by different routes. U.S. Pat. No. 4,322,271 (1982) discloses that N-vinyl-N-alkyl-carboxylic acid amides can be obtained by removing an alcohol from N-α-alkoxyethyl-N-alkyl-carboxylic acid amides which have been made by prior alkylation and alkoxylation steps from N-ethyl-carboxylic acid amides.

Sommerville, et. al., ACS. *Polymer Preprints*, (1983) 24, 12-13, discloses preparing N-vinylacetamide from acetamide and acetaldehyde dimethyl acetal. This process requires large excesses of the acetal, for example mole ratios of about 20 moles of acetal per mole of acetamide, in order to achieve practical yields and purities and is reported to fail in the corresponding reaction with formamide.

U.S. Pat. No. 4,567,300 (1986) discloses, on the other hand, reacting formamide with acetaldehyde over a basic catalyst to form N-(α-hydroxyethyl)-formamide instead of ethylidene bisformamide. This process is unattractive because it requires two discrete steps, plus the handling of a solid intermediate and the disposal of salts.

U.S. Pat. No. 4,670,591 (1987) describes the synthesis of N-(l-alkoxyethyl) formamide from a vinyl ether and formamide. While this process is said to be effective with either an acidic or basic catalyst, the vinyl ethers are very expensive starting materials.

German Patent DE3443463 (1986) describes making N-vinylformamide using 1-cyanoethyl formamide. This process has the disadvantage of generating hydrogen cyanide which is toxic.

The above processes as routes to the manufacture of poly(vinylamines) all have disadvantages including difficult catalyst removal, toxic byproduct formation, low conversions or catalyst deactivation. A commercial process which does not have these disadvantages has yet to be developed. Ethylidene bisformamide is still an attractive intermediate for the synthesis of N-vinylformamide as this product is stable and can be efficiently cracked thermally to form a 1:1 mixture of N-vinylformamide and formamide. Such a mixture can be purified by distillation as described in U.S. Pat. No. 4,578,515.

The preparation of ethylidene bisformamide using strong acid ion exchange resins as disclosed in U.S. Pat. No. 4,490,557, has the disadvantage that the strong acid catalyst residues must be removed from the ethylidene bisformamide product prior to purification and cracking. Otherwise unwanted side reactions and loss of N-vinylformamide due to acid catalyzed degradation in the cracking step are observed. The use of the solid polymer acid resins, on the other hand, allows the removal of salts and catalyst as a solid from the liquid product. Unfortunately, however, in the synthesis of ethylidene bisformamide the catalyst activity declines rapidly during the reaction, giving poor conversions. This is caused by the hydrolysis of formamide and neutralization of the catalyst with ammonia. Since water is produced in the synthesis of ethylidene bisformamide and high levels of formamide are required to drive the synthesis reaction, it is not feasible to suppress the formation of ammonia using prior art technology. The result is poor conversions and impure product, probably arising from unwanted acetaldehyde self-condensation reactions. It is highly desirable, therefore, to find a way of improving the yields of ethylidene bisformamide in such reactions and reducing the loss of formamide by hydrolysis.

U.S. Patent 3,188,319 discloses a process for transesterifying vinyl esters by transesterifying lower vinyl esters with a higher molecular weight carboxylic acid in the presence of a salt of a metal of the platinum group. The patent teaches the use of mercury salts is undesirable for such transesterification reactions. Additionally, U.S. Pat. No. 4,425,277 teaches a transesterification reaction for the preparation of vinyl esters in the presence of a binary catalyst system comprising a man catalyst of a palladium compound.

Takase, et al., in a paper submitted to the Institute of Chemistry, College of General Education, Osaka University (Received Oct. 11, 1967) describes the reaction of a fatty amide and vinyl acetate to produce ethylidene bisamide, using stannic salt as a catalyst in the presence of a large excess of vinyl acetate.

Busse, et al. *J. Organometalic Chem* (1977) 140, 229-236 disclose vinyl ether transvinylation with alcohols catalyzed by complexes of platinum dichloride. Even at room temperature, acetal formation was observed for this reaction.

Bayer, et al. *Angew. Chem. Int. Ed. Engl.* (1979) 18(7), 533-534 disclose a reaction for the synthesis of N-vinyl imides using a large excess of vinyl acetate. i.e., about 27:1 over a sodium tetrachloropalladate catalyst.

BRIEF SUMMARY OF THE INVENTION

The present invention is a process for the production of ethylidene bisamide by reacting vinyl acetate with a primary carboxylic acid amide. The reaction is catalyzed by a salt of palladium(II), platinum(II) or mercury(II) and is carried out in the presence of an aliphatic or arylaliphatic alcohol in a concentration greater than 0.01 equivalents based upon the limiting reagent. In a preferred embodiment, vinyl acetate is reacted with formamide to produce ethylidene bisformamide and N-(1-alkoxyethyl)formamide as coproducts.

The addition of even a small amount of alcohol to the reaction system results in improved reactant conversion without a significant loss in selectivity.

DETAILED DESCRIPTION OF THE INVENTION

The present invention is a process for producing ethylidene bisamide by reacting vinyl acetate with a primary carboxylic acid amide. The reaction is carried out by mixing vinyl acetate, an alcohol and an amide in the presence of a catalyst in a stirred tank reactor. Suitable amides include those having the formula $R^2CONHR^1$ wherein $R^1$ and $R^2$ are independently H, $C_1$-$C_{10}$ alkyl or aryl, with formamide (i.e. $R^1$ and $R^2$ are H) being preferred to produce ethylidene bisformamide as product. The vinyl acetate to amide ratio should typically be from about 10:1 to 1:10, with a preferred ratio being 1:1-4. By adding alcohol to the reaction mixture, an increase in conversion is obtained without a significant decrease in selectivity, and in fact, an increase in selectivity is often realized. Additionally, N-(1-alkoxyethyl)amide is typically formed as a coproduct along with the ethylidene bisamide, both of which are precursors to N-vinylamide.

The reaction is catalyzed by a salt of palladium(II), platinum(II) or mercury(II), present in a concentration from about 0.1 to 10 mole % catalyst vs the limiting reagent, with a concentration from 1 to 3 mole % being preferred. Examples of suitable catalysts include the halides $PdX_2$, $PtX_2$ and $HgX_2$ where X is Cl, Br or I, and also the anionic halide complexes $M_2PdX_4$, and $M_2PtX_4$ where M is Li, Na, K or Cs and X is Cl or Br. Additionally, the neutral complexes $PdCl_2(RCN)_2$ and $PtCl_2(RCN)_2$ where R is $C_1$-$C_6$ alkyl or phenyl, are especially well suited. It has also been found that the palladium catalysts operate most efficiently in the presence of copper halides, particularly $CuCl_2$. Preferably, the catalysts should not be subjected to prolonged heating in the absence of one or more of the reactants. Moderately polar solvents such as acetonitrile and nitromethane may be used but are not required, and it has been found that $PtCl_2$ and acetonitrile produce especially good results.

The addition of an aliphatic or arylaliphatic alcohol to the reaction mixture improves the conversion without a significant loss of selectivity and in many instances actually improves selectivity toward the desired products. The alcohol should be present in the reaction mixture in a concentration greater than 0.01 equivalent based upon the limiting reagent, with a range from 0.05 to 10 equivalents generally being preferred. The limiting reagent can be vinyl acetate or formamide, whichever is present in a lesser amount on a mole basis. Examples of suitable alcohols include methanol, ethanol. 2-propanol, tertbutanol, isoamyl alcohol, isobutyl alcohol, neopentyl alcohol and benzyl alcohol, with 2-propanol being preferred.

The reaction is carried out at a temperature from about 0°-150° C. with a preferred range of 60°-100° C. and typically at atmospheric or autogeneous pressure, with atmospheric being preferred. Typically the reaction is carried out in a stirred tank reactor and 1-8 hours reaction time. While the reaction is not extremely oxygen sensitive, it is preferred to use an inert atmosphere such as argon or nitrogen.

EXPERIMENTAL

Unless otherwise indicated, the following experimental procedure was carried out for the following examples. To a 25 ml 3 neck roundbottom flask equipped with reflux condenser/gas inlet, mechanical stirrer, and rubber septum was charged successively catalyst, primary carboxylic acid amide, vinyl acetate and an alcohol. The vigorously stirred mixture was heated at 80° C. for 3 hrs under a slow argon purge. Unless otherwise stated all % yields are relative to vinyl acetate as the limiting reagent. N-vinylformamide (NVF) is formed in small amounts during gas chromatographic analysis of the reaction mixture. Product selectivity is defined as % yields (Bis+NVF +$CH_3CH(OR)NHCHO$+$CH_3CH(OR)_2$)/vinyl acetate conversion. The compounds ethylidene bisformamide (Bis), $CH_3CH(NHCHO)_2$, N-vinylformamide (NVF). $CH_2$=CHNHCHO, and N-(1-alkoxyethyl)formamide, $CH_3CH(OR)NHCHO$ are the desired products. The acetal $CH_3CH(OR)_2$ is not a direct NVF precursor but can be recycled back into the reactor.

EXAMPLE 1

Runs were carried out to determine the effect of the addition of 10 mole % alcohol on catalyst activity for the reaction of formamide (2.500 g, 55.5 mmol) with vinyl acetate (1.593 g, 18.5 mmol) under the reaction conditions set out below.

TABLE 1

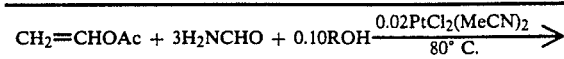

$$CH_2=CHOAc + 3H_2NCHO + 0.10ROH \xrightarrow[80° C.]{0.02PtCl_2(MeCN)_2}$$

| Time (hr) | % Yields NVF | Bis | Vinyl Acetate Conversion | Product Selectivity | ROH |
|---|---|---|---|---|---|
| 4 | 2-3 | 35-39 | 49-59 | 72-76 | None |
| 3 | 0 | 49 | 93 | 53 | MeOH |
| 4 | 0 | 67-71 | 100 | 67-71 | EtOH |
| 3 | 0-1 | 73-80 | 99-100 | 73-82 | i-PrOH |
| 3 | 0 | 64 | 94 | 68 | t-BuOH |

TABLE 1-continued reaction conditions and results are set out in Table 2 below.

TABLE 2

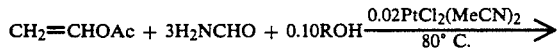

Catalyst 1 = PtCl$_2$(MeCN)$_2$;
Catalyst 2 = K$_2$PtCl$_4$;
Catalyst 3 = 0.02 PtCl$_2$/0.10 MeCN;
Catalyst 4 = 0.02 PdCl$_2$/0.05 CuCl$_2$

| Catalyst # | i-PrOH x | Temp (°C.) | % Yields CH$_3$CH(O-i-Pr)$_2$ | Bis | NVF | CH$_3$CH(O-i-Pr)NHCHO | Vinyl Acetate Conversion | Product Selectivity |
|---|---|---|---|---|---|---|---|---|
| 1 | 0 | 80 | 0 | 35–39 | 2–3 | 0 | 49–59 | 72–76 |
| 2 | 0 | 80 | 0 | 4 | 0.4 | 0 | 41 | 11 |
| 1 | 0.01 | 80 | 0 | 35 | 0.7 | 0 | 59 | 60 |
| 3 | 0.01 | 80 | 0 | 16 | 0.4 | 0 | 47 | 35 |
| 1 | 0.10 | 80 | 0 | 73–80 | 0–1 | 1 | 99–100 | 73–82 |
| 2 | 0.10 | 80 | 0 | 39 | 2 | 2 | 79 | 54 |
| 1 | 0.60 | 80 | 0 | 61 | 7 | 8 | 100 | 76 |
| 2 | 0.60 | 80 | 0.6–1 | 33–34 | — | 31 | 92–94 | 70–71 |
| 1 | 1.00 | 80 | 0 | 51 | — | 37 | 100 | 87 |
| 2 | 1.00 | 80 | 4 | 13 | — | 50 | 92 | 67 |
| 1 | 1.50 | 80 | 0.2 | 20–24 | — | 52–60 | 100 | 76–81 |
| 2 | 1.50 | 80 | 11 | 6 | — | 49 | 93 | 71 |
| 3 | 1.50 | 80 | 0.2 | 22 | — | 60 | 100 | 83 |
| 4 | 1.50 | 60 | 0.4 | 31 | — | 53 | 100 | 84 |
| 1 | 2.00 | 80 | 0.8 | 14 | — | 64 | 100 | 79 |
| 2 | 3.00 | 80 | 38 | 1 | — | 34 | 96 | 76 |
| 4 | 3.00 | 60 | 2 | 10 | — | 67 | 100 | 79 |
| 4 | 4.00 | 60 | 6 | 6 | — | 60 | 100 | 73 |

$$CH_2=CHOAc + 3H_2NCHO + 0.10ROH \xrightarrow[80°\,C.]{0.02PtCl_2(MeCN)_2}$$

| Time (hr) | % Yields NVF | % Yields Bis | Vinyl Acetate Conversion | Product Selectivity | ROH |
|---|---|---|---|---|---|
| 3 | 0 | 27 | 56 | 48 | CF$_3$CH$_2$OH |
| 3 | 0 | 24 | 55 | 44 | (CF$_3$)$_2$CHOH |
| 3 | 0 | 22 | 48 | 46 | C$_6$H$_5$OH |
| 4 | 2 | 39 | 59 | 70 | 1 equiv. CH$_3$COOH |

The above results demonstrate that addition of 10 mole % of an aliphatic alcohol vs. vinyl acetate roughly doubles catalyst activity while maintaining selectivities to Bis comparable to those obtained in the absence of an alcohol. Fluorinated and aromatic alcohols did not increase conversion and did lower selectivity, although a wide range of aromatic alcohols was not screened. For the above reaction, isopropanol is the preferred alcohol. In contrast, addition of one equivalent of acetic acid (vs. vinyl acetate) did not improve activity or selectivity, even though carboxylic acids are known to transvinylate readily with vinyl acetate.

EXAMPLE 2

Runs were carried out to determine the effect of isopropanol to vinyl acetate ratio on product distribution for the reaction of Example 1. The catalyst system, reaction conditions and results are set out in Table 2 below.

The above results show that for the PtCl$_2$(MeCN)$_2$ catalyst the level of isopropanol can be varied over a wide range without adversely affecting conversion or selectivity, although the ratio of the desired products, Bis and CH$_3$CH(O-i-Pr)NHCHO, can be varied from ~7:1 at 0.6 i-PrOH to ~1:4 at 2.0 i-PrOH. Isopropanol levels of 0.01. however, were generally ineffective and therefore the alcohol level for the reaction should be greater than 0.01 equivalents. The amount of CH$_3$CH(O-i-Pr)$_2$ (acetal) to be recycled is held to a minimum in all cases. In contrast, K$_2$PtCl$_4$ affords comparable activities at x=0.60 i-PrOH or higher, but selectivity is lower and acetal yield is correspondingly greater in all cases. PdCl$_2$/CuCl$_2$ is comparable to PtCl$_2$(MeCN)$_2$ but favors Bis formation at 1.5 i-PrOH.

EXAMPLE 3

Runs were carried out to determine the effect of Formamide to vinyl acetate ratio on product distribution for the reaction of formamide with vinyl acetate. In this Example, y was chosen to correspond to the amount of isopropanol which afforded high CH$_3$CH(O-i-Pr)NHCHO yields and product selectivities with 3 equivalents of formamide (Example 2). The formamide level was then varied with the vinyl acetate to isopropanol ratio fixed. The reaction conditions, catalyst systems and results are set out in Table 3 below.

TABLE 3

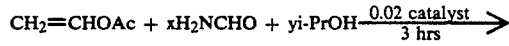

Catalyst 1 = PtCl$_2$(MeCN)$_2$, y = 1.5;
Catalyst 2 = K$_2$PtCl$_4$, y = 1.0;
Catalyst 3 = 0.02 PtCl$_2$/0.10 MeCN, y = 1.5;
Catalyst 4 = 0.02 PdCl$_2$/0.05 CuCl$_2$, y = 3.0.

| Catalyst # | H$_2$NCHO x | Temp (°C.) | % Yields CH$_3$CH(O-i-Pr)$_2$ | Bis | CH$_3$CH(O-i-Pr)NHCHO | Vinyl Acetate Conversion | Product Selectivity |
|---|---|---|---|---|---|---|---|
| 1 | 4 | 80 | 0.2 | 30 | 55 | 100 | 86 |
| 2 | 4 | 80 | 0.4 | 29 | 43 | 98 | 73 |
| 4 | 4 | 60 | 0.7 | 15 | 64 | 100 | 80 |
| 1 | 3 | 80 | 0.2 | 20–24 | 52–60 | 100 | 76–81 |

TABLE 3-continued $$CH_2=CHOAc + xH_2NCHO + y\text{i-PrOH} \xrightarrow[3 \text{ hrs}]{0.02 \text{ catalyst}}$$

Catalyst 1 = PtCl$_2$(MeCN)$_2$, y = 1.5;
Catalyst 2 = K$_2$PtCl$_4$, y = 1.0;
Catalyst 3 = 0.02 PtCl$_2$/0.10 MeCN, y = 1.5;
Catalyst 4 = 0.02 PdCl$_2$/0.05 CuCl$_2$, y = 3.0.

| Catalyst # | H$_2$NCHO x | Temp (°C.) | % Yields CH$_3$CH(O-i-Pr)$_2$ | Bis | CH$_3$CH(O-i-Pr)NHCHO | Vinyl Acetate Conversion | Product Selectivity |
|---|---|---|---|---|---|---|---|
| 2 | 3 | 80 | 2–4 | 13–17 | 50–51 | 92–96 | 67–73 |
| 3 | 3 | 80 | 0.2 | 22 | 60 | 100 | 83 |
| 4 | 3 | 60 | 2 | 10 | 67 | 100 | 79 |
| 1 | 2 | 80 | 0.3 | 20 | 61 | 100 | 81 |
| 2 | 2 | 80 | 4 | 11 | 48 | 93 | 68 |
| 3 | 2 | 80 | 1 | 15 | 61 | 100 | 77 |
| 1 | 1.5 | 80 | 0.9 | 17 | 62 | 100 | 80 |
| 3 | 1.5 | 80 | 2 | 12 | 62 | 100 | 77 |
| 4 | 1.5 | 60 | 4 | 10 | 63 | 100 | 76 |
| 1 | 1 | 80 | 7 | 10 | 63 | 100 | 80 |
| 3* | 0.4 | 80 | 27 | 1 | 29 | 100 | 70 |
| 3** | 0.4 | 80 | 7 | 3 | 21 | 71 | 64 |
| 3* | 1 | 80 | 16 | 5 | 57 | 100 | 83 |
| 3 | 1 | 80 | 11 | 6 | 59 | 100 | 79 |

*Time = 1 hr.
**y = 0.6

The above results show that for the PtCl$_2$(MeCN)$_2$ catalyst the formamide level can be lowered from a 4:1 excess vs. vinyl acetate to a 1:1 ratio without adversely affecting selectivity. The ratio of CH$_3$CH(O-i-Pr)NHCHO to Bis varies from ~1.8:1 to ~6.3:1 as the formamide level is decreased. Only at the 1:1 vinyl acetate to formamide ratio did formation of the acetal byproduct start to become appreciable. Additionally, the above results (last 4 entries) show that the formamide to vinyl acetate ratio can be decreased from 1:1 to 1:2.5 and reasonable activities and selectivities are still obtained. However, with formamide as the limiting reagent more recycle of acetaldehyde diisopropyl acetal (CH$_3$CH(O-i-Pr)$_2$) is necessary. This compound can be converted to i-PrEF and Bis, so they are not yield losses. Essentially either vinyl acetate or formamide can be used as the limiting reagent, although the selectivity is somewhat lower when the vinyl acetate to formamide ratio exceeds 1. This trend can be compensated for by increasing the amount of isopropanol (compare y=0.6 and y=1.5 entries) but this also increases recycle.

K$_2$PtCl$_4$ afforded somewhat lower selectivity. The PtCl$_2$/MeCN mixture is comparable to pure PtCl$_2$(MeCN)$_2$ and PtCl$_2$ is the less expensive metal source. The PdCl$_2$/CuCl$_2$ catalyst consistently afforded higher CH$_3$CH(O-i-Pr)NHCHO to Bis ratios than the platinum catalysts, with comparable selectivities. This latitude in stoichiometry permits the adjustment of the residual formamide level. Formamide content can affect product purification and stability and some variability in this level is desirable.

EXAMPLE 4

Runs were carried out to determine the effect of the addition of alcohol on product distribution for the reaction of formamide with vinyl acetate. The reaction conditions, catalyst systems and results are presented in Table 4 below.

TABLE 4

$$CH_2=CHOAc + 3H_2NCHO + yROH \xrightarrow[80° C., 3 \text{ hrs}]{0.02 \text{ catalyst}}$$

Catalyst 1 = PtCl$_2$(MeCN)$_2$, y = 1.5;
Catalyst 2 = K$_2$PtCl$_4$, y = 1.0;
Catalyst 4 = 0.02 PdCl$_2$/0.05 CuCl$_2$, y = 1.5, temp = 60° C.

| Catalyst # | ROH | % Yields CH$_3$CH(OR)$_2$ | Bis | NVF | CH$_3$CH(OR)NHCHO | Vinyl Acetate Conversion | Product Selectivity |
|---|---|---|---|---|---|---|---|
| 1 | EtOH | 19 | 5 | 0.4 | 37 | 99 | 61 |
| 2 | EtOH | 10 | 6 | 1 | 31 | 91 | 53 |
| 4 | EtOH | 5 | 15 | 5 | 40 | 100 | 65 |
| 1 | i-PrOH | 0.2 | 20–24 | — | 52–60 | 100 | 76–81 |
| 2 | i-PrOH | 4 | 13 | — | 50 | 92 | 67 |
| 4 | i-PrOH | 0.4 | 31 | — | 53 | 100 | 84 |
| 1 | EtMe$_2$COH | 0 | 83 | 1 | 0 | 100 | 84 |
| 2 | EtMe$_2$COH | 0 | 28 | 2 | ~4 | 62 | 48 |
| 1 | Me$_2$CHCH$_2$OH | 20 | 18 | 0.5 | 10 | 99 | 28 |
| 1 | Me$_3$CCH$_2$OH | 31 | 24 | 0.5 | 10 | 100 | 35 |
| 1 | PhCH$_2$OH | 13 | 2 | 0.4 | 3 | 76 | 7 |

The above results show that the addition of alcohol, and in particular isopropanol is well suited to maintaining high product selectivity while minimizing formation of acetal byproduct. Placing too little (EtOH) or too much (EtMe$_2$COH) steric hindrance on the -OH containing carbon lowers selectivity somewhat for K$_2$PtCl$_4$. With PtCl$_2$(MeCN)$_2$, EtMe$_2$COH affords exclusively Bis with a selectivity comparable to those obtained with i-PrOH. Thus CH$_3$CH(OR)NHCHO formation can be eliminated if desired while still realizing the rate and selectivity enhancements obtained with less hindered alcohols. Isopropanol is also preferable to ethanol when using the $PdCl_2/CuCl_2$ catalyst. For $PtCl_2(MeCN)_2$, moving the alkyl substituents to the carbon α to the hydroxyl bearing carbon ($Me_2CHCH_2OH$, $Me_3CCH_2OH$) lowers selectivity and results in more acetal formation. $PhCH_2OH$ also lowers selectivity, although this is probably due to electronic rather than steric effects.

EXAMPLE 5

Runs were carried out to determine the effect of various nitriles on product distribution for the reaction of formamide with vinyl acetate in the presence of an alcohol. The specific nitriles, reaction conditions and results are reported in Table 5 below.

TABLE 5

$$CH_2=CHOAc + 3H_2NCHO + 1.5\text{i-PrOH} + xRCN \xrightarrow[80° C., 3 \text{ hrs}]{0.02 \text{ catalyst}}$$

Catalyst 1 = $PtCl_2(MeCN)_2$;
Catalyst 2 = $K_2PtCl_4$;
Catalyst 3 = $PtCl_2$;
Catalyst 4 = 0.02 $PdCl_2$/0.05 $CuCl_2$, temp = 60° C.

| Catalyst # | $CH_3CN$ x | % Yields $CH_3CH(O-i-Pr)_2$ | Bis | $CH_3CH(O-i-Pr)NHCHO$ | Vinyl Acetate Conversion | Product Selectivity |
|---|---|---|---|---|---|---|
| 1 | 0 | 0.2 | 20–24 | 52–60 | 100 | 76–81 |
| 2 | 0 | 11 | 6 | 49 | 93 | 71 |
| 3 | 0 | 1 | 17 | 41 | 90 | 66 |
| 4 | 0 | 0.4 | 31 | 53 | 100 | 84 |
| 2 | 0.04 | 9 | 8 | 54 | 97 | 74 |
| 3 | 0.04 | 0.5 | 19 | 59 | 100 | 79 |
| 2 | 0.10 | 9 | 9 | 56 | 98 | 75 |
| 3 | 0.10 | 0.2 | 22 | 60 | 100 | 83 |
| 2 | 0.50 | 8 | 10 | 60 | 98 | 80 |
| 3 | 0.50 | 0.2 | 25 | 60 | 100 | 85 |
| 1 | 1.00 | 0.3 | 25 | 59 | 100 | 84 |
| 2 | 1.00 | 7 | 11 | 62 | 99 | 80 |
| 3 | 1.00 | 0.4 | 22 | 65 | 100 | 87 |
| 4 | 1.00 | 0.5 | 34 | 49 | 99 | 83 |
| 3 | $C_6F_5CN$ 0.10 | 8 | 10 | 56 | 96 | 77 |
| 3 | $Me_3CCN$ 0.10 | 0.7 | 15 | 58 | 99 | 75 |
| 3 | $NC(CH_2)_4CN$ 0.50 | 0.2 | 28 | 58 | 100 | 87 |
| 3 | $n\text{-}C_{11}H_{23}CN$ 1.00 | 1.7 | 25 | 52 | 99 | 80 |

The above results show that the selectivity obtained with the $K_2PtCl_4$ catalyst can be improved from 71 to 80% by adding up to 1 equivalent of acetonitrile per equivalent of vinyl acetate. Acetonitrile showed essentially no effect on the performance of the $PtCl_2(MeCN)_2$ and $PdCl_2/CuCl_2$ catalysts. The selectivity obtained with $PtCl_2$ increased from 66 to 87% with the addition of acetonitrile. Thus performance equivalent to that of $PtCl_2(MeCN)_2$ is obtained with a cheaper platinum source. Other nitriles did not strongly influence the performance of $PtCl_2$.

EXAMPLE 6

The reaction of formamide with vinyl acetate in the presence of an alcohol was carried out using various catalyst systems. The specific catalyst systems along with the reaction conditions and results are reported in Table 6 below.

TABLE 6

$$CH_2=CHOAc + 3H_2NCHO + 1.0\text{i-PrOH} \xrightarrow[80° C., 3 \text{ hrs}]{0.02 \text{ catalyst}}$$

| Catalyst | % Yields $CH_3CH(O-i-Pr)_2$ | Bis | $CH_3CH(O-i-Pr)NHCHO$ | Vinyl Acetate Conversion | Product Selectivity |
|---|---|---|---|---|---|
| $KPtCl_3(C_2H_4).H_2O$ | 3 | 12 | 49 | 94 | 68 |
| $Na_2PtCl_4.0.66H_2O$ | 4 | 12 | 46 | 89 | 69 |
| $Cs_2PtCl_4.0.24H_2O$ | 7 | 7 | 45 | 87 | 68 |
| $K_2PtBr_4$ | 3 | 13 | 45 | 88 | 68 |
| $PtCl_2$ | 1 | 17 | 41 | 90 | 66 |
| $PtCl_4$ | 2 | 4 | 16 | 69 | 30 |
| $K_2PdCl_4(3.0\text{i-PrOH})$ | 4 | 7 | 54 | 95 | 66 |

The above results demonstrate that other halide complexes of platinum(II) are comparable to $K_2PtCl_4$, but $PtCl_2(MeCN)_2$ is still preferred. $PtCl_4$ also showed some activity but selectivity was relatively poor.

EXAMPLE 7

Runs were carried out to determine the effect of various copper (II) cocatalyst on $PdCl_2$ selectivity for the reaction of formamide with vinyl acetate.

The specific cocatalyst along with the reaction conditions and results are reported in Table 7 below.

TABLE 7

$$CH_2=CHOAc + 3H_2NCHO + 3i\text{-}PrOH \xrightarrow[60°\text{ C., 3 hrs}]{0.02\ PdCl_2}$$

| Cu Salt (mole %) | % Yields | | | Vinyl Acetate Conversion | Product Selectivity |
| --- | --- | --- | --- | --- | --- |
| | $CH_3CH(O\text{-}i\text{-}Pr)_2$ | Bis | $CH_3CH(O\text{-}i\text{-}Pr)NHCHO$ | | |
| None | 10 | 4 | 63 | 99 | 78 |
| $CuCl_2$ (5.0) | 2 | 10 | 67 | 100 | 79 |
| $CuCl_2.2H_2O$ (5.0) | 4 | 7 | 68 | 100 | 80 |
| $CuBr_2$ (5.0) | 11 | 8 | 55 | 98 | 74 |
| $CuF_2.2H_2O$ (5.0) | 1 | 0 | 22 | 37 | 60 |
| $Cu(NO_3)_2.3H_2O$ (5.0) | 0.5 | 21 | 46 | 95 | 68 |
| $Cu(O_3SCF_3)_2$ (5.0) | 0.7 | 2 | 62 | 100 | 65 |
| $Cu(OAc)_2.H_2O$ (5.0) | 0.4 | 0 | 16 | 30 | 53 |
| $Cu_3(PO_4)_2$ (1.67) | 24 | 1 | 40 | 82 | 79 |
| $CuSO_4.5H_2O$ (5.0) | 5 | 4 | 56 | 97 | 67 |

The above results show that cupric chloride and bromide afforded superior activities and selectivities without evidence of palladium metal formation. Cupric phosphate was comparably selective but formed appreciable quantities of acetal. Palladium chloride alone was as effective but extensive reduction to the metal occurred.

The novel feature of this invention is that although reaction of alcohols with vinyl acetate to afford vinyl ethers and acetals is known to be rapid even below 0° C., the preferred platinum and palladium catalysts afford only small amounts of acetal. In some cases increasing the amount of alcohol actually improves the selectivity to amide containing products. Carboxylic acids are known to transvinylate readily, but as shown in Example 1, final entry, addition of one equivalent of acetic acid (vs. vinyl acetate) to a vinyl acetate/formamide mixture does not improve activity or selectivity. Thus all substrates known to readily undergo transvinylation are not equally effective at increasing the activity and selectivity of the platinum and palladium catalysts.

What is claimed is:

1. A process for the production of ethylidene bisamide comprising reacting vinyl acetate with a primary carboxylic acid amide over a catalyst comprising a salt of palladium(II), platinum(II) or mercury(II) in the presence of greater than 0.01 equivalents of an aliphatic or arylaliphatic alcohol based upon the limiting reagent.

2. A process in accordance with claim 1 wherein said primary carboxylic acid amide is present in a concentration of from 1 to 4 equivalents based upon vinyl acetate.

3. A process in accordance with claim 1 wherein said catalyst is present in a concentration of from 0.1 to 10 mole % based upon the limiting reagent.

4. A process in accordance with claim 1 which is carried out at a temperature from 0° to 150° C.

5. A process in accordance with claim 1 which is carried out at atmospheric or autogeneous pressure.

6. A process in accordance with claim 1 which is carried out for a reaction time from 1 to 8 hours.

7. A process in accordance with claim 1 which is carried out in an inert atmosphere.

8. A process in accordance with claim 1 which is carried out in the presence of a moderately polar solvent.

9. A process in accordance with claim 8 wherein said moderately polar solvent is acetonitrile or nitromethane.

10. A process in accordance with claim 1 wherein ethylidene bisformamide is produced by reacting vinyl acetate with formamide.

11. A process in accordance with claim 1 wherein said alcohol is selected from the group consisting of methanol, ethanol, 2-propanol, tertbutanol, isoamyl alcohol, isobutyl alcohol, neopentyl alcohol, benzyl alcohol and mixtures thereof.

12. A process in accordance with claim 11 wherein said alcohol is 2-propanol.

13. A process in accordance with claim 1 wherein said primary carboxylic acid amide has the structural formula $R^2CONHR^1$ wherein $R^1$ and $R^2$ are independently H, $C_1$–$C_{10}$ alkyl or aryl.

14. A process in accordance with claim 1 wherein said reaction is carried out in the presence of from 0.05 to 10 equivalents of an aliphatic or arylaliphatic alcohol based upon the limiting reagent.

15. A process in accordance with claim 1 wherein said catalyst is selected from $PdX_2$, $PtX_2$, $M_2PdX_4$ and $M_2PtX_4$ wherein X is Cl, Br or I and M is Li, Na, K or Cs.

16. A process in accordance with claim 1 wherein said catalyst is a neutral complex of Pd or Pt having the formula $PdCl_2(RCN)_2$ or $PtCl_2(RCN)_2$ wherein R is $C_1$–$C_6$ alkyl or phenyl.

17. A process in accordance with claim 1 wherein said catalyst also comprises a copper halide compound.

18. A process in accordance with claim 17 wherein said copper halide is $CuCl_2$.

* * * * *